(12) United States Patent
Chiu et al.

(10) Patent No.: US 6,686,471 B2
(45) Date of Patent: Feb. 3, 2004

(54) PROCESS AND INTERMEDIATES FOR GROWTH HORMONE SECRETAGOGUES

(75) Inventors: Charles K. Chiu, Guilford, CT (US); David A. Griffith, Old Saybrook, CT (US)

(73) Assignee: Pfizer Inc., New York, NY (US)

( * ) Notice: Subject to any disclaimer, the term of this patent is extended or adjusted under 35 U.S.C. 154(b) by 0 days.

(21) Appl. No.: 10/456,405

(22) Filed: Jun. 5, 2003

(65) Prior Publication Data

US 2003/0225280 A1 Dec. 4, 2003

Related U.S. Application Data

(62) Division of application No. 10/209,834, filed on Jul. 31, 2002, now Pat. No. 6,603,002, which is a division of application No. 09/922,040, filed on Aug. 3, 2001, now Pat. No. 6,465,651, which is a division of application No. 09/438,911, filed on Nov. 12, 1999, now Pat. No. 6,297,380.
(60) Provisional application No. 60/109,524, filed on Nov. 23, 1998.

(51) Int. Cl.⁷ .............................................. C07D 487/04
(52) U.S. Cl. ..................................................... 544/350
(58) Field of Search ........................................ 544/350

(56) References Cited

U.S. PATENT DOCUMENTS

| | | | |
|---|---|---|---|
| 4,746,755 A | 5/1988 | Paul et al. | 562/450 |
| 4,868,061 A | 9/1989 | Cesa et al. | 526/258 |
| 5,929,243 A | 7/1999 | Askin et al. | 546/227 |
| 6,251,902 B1 * | 6/2001 | Carpino et al. | |
| 6,297,380 B1 | 10/2001 | Chiu et al. | 544/350 |
| 6,358,951 B1 | 3/2002 | Carpino | 514/248 |
| 6,429,313 B2 * | 8/2002 | Carpino et al. | |
| 6,433,171 B1 * | 8/2002 | Carpino et al. | |
| 6,465,651 B2 | 10/2002 | Chiu et al. | 544/350 |
| 6,525,047 B2 * | 2/2003 | Carpino et al. | |

FOREIGN PATENT DOCUMENTS

| | | |
|---|---|---|
| DE | 3643748 | 6/1988 |
| WO | WO 9724369 | 7/1997 |
| WO | WO 9858947 | 12/1998 |

OTHER PUBLICATIONS

Iwata, et al. "Novel Syntheses of Hydantoin Derivatives", *J. Heterocyclic Chem.* 15, pp. 1231–1234 (1978).
Capuano, et al. "Neue Hydantoine Mit Brueckenknopf–Stickstoff bzw. Spiran–Struktur", *Chem. Ber.* 103, pp. 2394–2402 (1970).
Jucker, et al., "C–Substituted Piperazine Derivatives", *Helv. Chim. Acta* 273, pp. 2383–2402 (1961).
Lopez, et al. "The Chemisty of Hydantoins", *Adv. Heterocycl. Chem.* 38, pp. 178–228 (1985).
Khandelwal, et al. Agents Acting on CNS: Part XXXV—Synthesis of Imidazo[I,5–a]pyrazines & Pyrazino[I,2–a]pyrazines, *Indian Journal of Chemistry* 16B, pp. 1015–1018 (1978).

\* cited by examiner

*Primary Examiner*—Emily Bernhardt
(74) *Attorney, Agent, or Firm*—Peter C. Richardson; Gregg C. Benson; Martha G. Munchhof

(57) ABSTRACT

This invention relates to a process for preparing compounds of the Formula I,

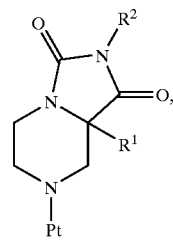

wherein $R^1$, $R^2$ and Pt are as defined in the specification, which are intermediates in the synthesis of certain growth hormone secretagogue compounds. This invention further relates to processes for preparing the growth hormone secretagogues. The invention also relates to the compound of Formula I wherein $R^1$ is H, $R^2$ is 2,2,2-trifluoromethyl and Pt is Boc.

5 Claims, No Drawings

PROCESS AND INTERMEDIATES FOR GROWTH HORMONE SECRETAGOGUES

CROSS-REFERENCE TO RELATED APPLICATION

This is a divisional application of U.S. Ser. No. 10/209,834, filed Jul. 31, 2002, now U.S. Pat. No. 6,603,002, which is a divisional application of U.S. Ser. No. 09/922,040, filed Aug. 3, 2001, now U.S. Pat. No. 6,465,651, which is a divisional of U.S. Ser. No. 09/438,911, filed Nov. 12, 1999, now U.S. Pat. No. 6,297,380, which claims the benefit from U.S. Provisional Application No. 60/109,524, filed Nov. 23, 1998.

BACKGROUND OF THE INVENTION

This invention relates to a process for preparing a compound of Formula I,

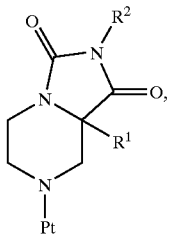

wherein $R^1$, $R^2$, and Pt are as defined below, which can be used to prepare certain growth hormone secretagogues of Formula II below. This invention also relates to processes for preparing said growth hormone secretagogues.

The compounds of Formula II wherein $R^1$ and $R^2$ are as defined below are potent growth hormone secretagogues. These compounds and their preparation have been disclosed in International patent publication WO98/58947.

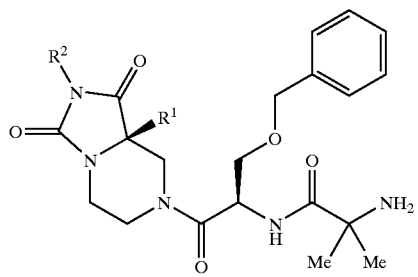

SUMMARY OF THE INVENTION

This invention is directed to a compound of Formula VII,

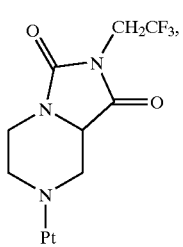

wherein
Pt is an amine protecting group.
A preferred compound of Formula VII is the compound wherein Pt is Boc.

This invention is also directed to a process, designated Process A, for preparing a compound of Formula III,

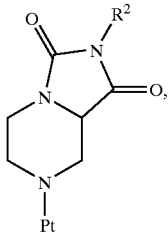

wherein
Pt is an amine protecting group;
$R^2$ is hydrogen, $(C_1–C_8)$alkyl, $—(C_0–C_3)$alkyl-$(C_3–C_8)$cycloalkyl, $—(C_1–C_4)$alkyl-$A^1$ or $A^1$;
$A^1$ for each occurrence is independently selected from the group consisting of $(C_5–C_7)$cycloalkenyl, phenyl, a partially saturated, fully saturated or fully unsaturated 4- to 8-membered ring optionally having 1 to 4 heteroatoms independently selected from the group consisting of oxygen, sulfur and nitrogen and a bicyclic ring system consisting of a partially saturated, fully unsaturated or fully saturated 5- or 6-membered ring, optionally having 1 to 4 heteroatoms independently selected from the group consisting of nitrogen, sulfur and oxygen, fused to a partially saturated, fully saturated or fully unsaturated 5- or 6-membered ring, optionally having 1 to 4 heteroatoms independently selected from the group consisting of nitrogen, sulfur and oxygen;
$A^1$ for each occurrence is independently optionally substituted, on one or optionally both rings if $A^1$ is a bicyclic ring system, with up to three substituents, each substituent independently selected from the group consisting of F, Cl, Br, I, $OCF_3$, $OCF_2H$, $CF_3$, $CH_3$, $OCH_3$, $—OX^6$, $—C(O)N(X^6)(X^6)$, $—C(O)OX^6$, oxo, $(C_1–C_6)$alkyl, nitro, cyano, benzyl, $—S(O)_m(C_1–C_6)$alkyl, 1H-tetrazol-5-yl, phenyl, phenoxy, phenylalkyloxy, halophenyl, methylenedioxy, $—N(X^6)(X^6)$, $—N(X^6)C(O)(X^6)$, $—S(O)_2N(X^6)(X^6)$, $—N(X^6)S(O)_2$-phenyl, $—N(X^6)S(O)_2X^6$, $—CONX^{11}X^{12}$, $—S(O)_2NX^{11}X^{12}$, $—NX^6S(O)_2X^{12}$, $—NX^6CONX^{11}X^{12}$, $—NX^6S(O)_2NX^{11}X^{12}$, $—NX^6C(O)X^{12}$, imidazolyl, thiazolyl and tetrazolyl, provided that if $A^1$ is optionally substituted with methylenedioxy then it can only be substituted with one methylenedioxy;
where $X^{11}$ is hydrogen or optionally substituted $(C_1–C_6)$alkyl;
the optionally substituted $(C_1–C_6)$alkyl defined for $X^{11}$ is optionally independently substituted with phenyl, phenoxy, $(C_1–C_6)$alkoxycarbonyl, $—S(O)_m(C_1–C_6)$alkyl, 1 to 5 halo groups, 1 to 3 hydroxy groups, 1 to 3 $(C_1–C_{10})$alkanoyloxy groups or 1 to 3 $(C_1–C_6)$alkoxy groups;
$X^{12}$ is hydrogen, $(C_1–C_6)$alkyl, phenyl, thiazolyl, imidazolyl, furyl or thienyl, provided that when $X^{12}$ is not hydrogen, the $X^{12}$ group is optionally substituted with one to three substituents independently selected from the group consisting of Cl, F, $CH_3$, $OCH_3$, $OCF_3$ and $CF_3$;
or $X^{11}$ and $X^{12}$ are taken together to form $—(CH_2)_r—L^1—(CH_2)_r—$;
$L^1$ is $C(X^2)(X^2)$, O, $S(O)_m$ or $N(X^2)$;

$X^6$ for each occurrence is independently hydrogen, optionally substituted $(C_1-C_6)$alkyl, $(C_2-C_6)$ halogenated alkyl, optionally substituted $(C_3-C_7)$ cycloalkyl, $(C_3-C_7)$-halogenated cycloalkyl, where optionally substituted $(C_1-C_6)$alkyl and optionally substituted $(C_3-C_7)$cycloalkyl in the definition of $X^6$ is optionally independently mono- or di-substituted with $(C_1-C_4)$alkyl, hydroxy, $(C_1-C_4)$alkoxy, carboxyl, $CONH_2$, $—S(O)_m(C_1-C_6)$alkyl, carboxylate $(C_1-C_4)$ alkyl ester or 1H-tetrazol-5-yl; or when there are two $X^6$ groups on one atom and both $X^6$ are independently $(C_1-C_6)$alkyl, the two $(C_1-C_6)$alkyl groups may be optionally joined and, together with the atom to which the two $X^6$ groups are attached, form a 4- to 9-membered ring optionally having oxygen, sulfur or $NX^7$ as a ring member;

r for each occurrence is independently 1, 2 or 3;
comprising reacting a compound of Formula IV,

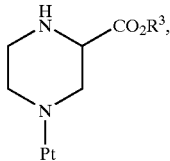

IV wherein $R^3$ is $(C_1-C_4)$alkyl and Pt is as defined above, with a preformed isocyanate or a carbonyl equivalent and $R^2NH_2$, wherein $R^2$ is as defined hereinabove, in a reaction inert solvent for about one hour to about 72 hours at a temperature of about 0° C. to about 80° C.

A preferred process within Process A, designated Process B, comprises the process wherein $R^2$ is hydrogen, $(C_1-C_8)$ alkyl or $—(C_0-C_3)$alkyl-$(C_3-C_8)$cycloalkyl; where the alkyl groups and the cycloalkyl groups in the definition of $R^2$ are optionally substituted with 1, 2 or 3 fluorine and wherein Pt is tert-butyloxycarbonyl.

A preferred process within Process B, designated Process C, comprises the process wherein said compound of Formula IV is reacted with a carbonyl equivalent selected from carbonyldiimidazole, phosgene, triphosgene and diphosgene.

A preferred process within Process C, designated Process D, comprises the process wherein said carbonyl equivalent is carbonyldiimidazole and said reaction inert solvent is methylene chloride.

A preferred process within Process D, designated Process E, comprises the process wherein $R^2$ is methyl, ethyl or 2,2,2-trifluoroethyl.

An especially preferred process within Process E is the process wherein $R^2$ is methyl.

Another especially preferred process within Process E is the process wherein $R^2$ is ethyl.

Yet another especially preferred process within Process E is the process wherein $R^2$ is 2,2,2-trifluoroethyl.

This invention is also directed to a process, designated Process F, for preparing a compound of Formula I,

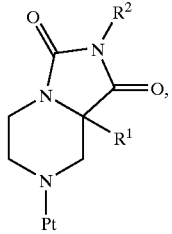

I wherein
$R^1$ is $—(CH_2)_qN(X^6)C(O)X^6$, $—(CH_2)_qN(X^6)C(O)$ $(CH_2)_t—A^1$, $—(CH_2)_qN(X^6)S(O)_2(CH_2)_t—A^1$, $—(CH_2)_qN(X^6)S(O)_2X^6$, $—(CH_2)_qN(X^6)C(O)N(X^6)$ $(CH_2)_t—A^1$, $—(CH_2)_qN(X^6)C(O)N(X^6)(X^6)$, $—(CH_2)_qC(O)N(X^6)(X^6)$, $—(CH_2)_qC(O)N(X^6)$ $(CH_2)_t—A^1$, $—(CH_2)_qC(O)OX^6$, $—(CH_2)_qC(O)O$ $(CH_2)_t—A^1$, $—(CH_2)_qOX^6$, $—(CH_2)_qOC(O)X^6$, $—(CH_2)_qOC(O)(CH_2)_t—A^1$, $—(CH_2)_qOC(O)N(X^6)$ $(CH_2)_t—A^1$, $—(CH_2)_qOC(O)N(X^6)(X^6)$, $—(CH_2)_qC$ $(O)X^6$, $—(CH_2)_qC(O)(CH_2)_t—A^1$, $—(CH_2)_qN(X^6)C$ $(O)OX^6$, $—(CH_2)_qN(X^6)S(O)_2N(X^6)(X^6)$, $—(CH_2)_qS$ $(O)_mX^6$, $—(CH_2)_qS(O)_m(CH_2)_t—A^1$, $—(C_1-C_{10})$alkyl, $—(CH_2)_q—A^{11}$, $—(CH_2)_q—(C_3-C_7)$cycloalkyl, $—(CH_2)_q—Y^1—(C_1-C_6)$alkyl, $—(CH_2)_q—Y^1—$ $(CH_2)_t—A^1$ or $—(CH_2)_q—Y^1—(CH_2)_t—(C_3-C_7)$ cycloalkyl;

where the alkyl and cycloalkyl groups in the definition of $R^1$ are optionally substituted with $(C_1-C_4)$alkyl, hydroxy, $(C_1-C_4)$alkoxy, carboxyl, $—CONH_2$, $—S(O)_m(C_1-C_6)$alkyl, $—CO_2(C_1-C_4)$alkyl ester, 1H-tetrazol-5-yl or 1, 2 or 3 fluoro groups;

$Y^1$ is O, $S(O)_m$, $—C(O)NX^6—$, $—CH=CH—$, $—C≡C—$, $—N(X^6)C(O)—$, $—C(O)NX^6—$, $—C(O)O—$, $—OC(O)N(X^6)—$ or $—OC(O)—$;

q is 1, 2, 3 or 4;
t is 0, 1, 2 or 3;
said $(CH_2)_q$ group and $(CH_2)_t$ group in the definition of $R^1$ are optionally independently substituted with hydroxy, $(C_1-C_4)$alkoxy, carboxyl, $—CONH_2$, $—S(O)_m(C_1-C_6)$alkyl, $—CO_2(C_1-C_4)$alkyl ester, 1H-tetrazol-5-yl, 1, 2 or 3 fluoro groups or 1 or 2 $(C_1-C_4)$alkyl groups; and $R^2$ is hydrogen, $(C_1-C_8)$alkyl, $—(C_0-C_3)$alkyl-$(C_3-C_8)$ cycloalkyl, $—(C_1-C_4)$alkyl-$A^1$ or $A^1$;
where the alkyl groups and the cycloalkyl groups in the definition of $R^1$ are optionally substituted with hydroxy, $—C(O)OX^6$, $—C(O)N(X^6)(X^6)$, $—N(X^6)$ $(X^6)$, $—N(X^6)X^6$, $—S(O)_m(C_1-C_6)$alkyl, $—C(O)A^1$, $—C(O)(X^6)$, $CF_3$, CN or 1, 2 or 3 independently selected halo groups;

$A^1$ for each occurrence is independently selected from the group consisting of $(C_5-C_7)$cycloalkenyl, phenyl, a partially saturated, fully saturated or fully unsaturated 4- to 8-membered ring optionally having 1 to 4 heteroatoms independently selected from the group consisting of oxygen, sulfur and nitrogen and a bicyclic ring system consisting of a partially saturated, fully unsaturated or fully saturated 5- or 6-membered ring, optionally having 1 to 4 heteroatoms independently selected from the group consisting of nitrogen, sulfur and oxygen, fused to a partially saturated, fully saturated or fully unsaturated 5- or 6-membered ring, optionally having 1 to 4 heteroatoms independently selected from the group consisting of nitrogen, sulfur and oxygen;

$A^1$ for each occurrence is independently optionally substituted, on one or optionally both rings if $A^1$ is a bicyclic ring system, with up to three substituents, each substituent independently selected from the group consisting of F, Cl, Br, I, $OCF_3$, $OCF_2H$, $CF_3$, $CH_3$, $OCH_3$, $—OX^6$, $—C(O)N(X^6)(X^6)$, $—C(O)$ $OX^6$, oxo, $(C_1-C_6)$alkyl, nitro, cyano, benzyl, $—S(O)_m(C_1-C_6)$alkyl, 1H-tetrazol-5-yl, phenyl, phenoxy, phenylalkyloxy, halophenyl, methylenedioxy, $—N(X^6)(X^6)$, $—N(X^6)C(O)(X^6)$, $—S(O)_2N(X^6)(X^6)$, $—N(X^6)S(O)_2$-phenyl, $—N(X^6)$ $S(O)_2X^6$, $—CONX^{11}X^{12}$, $—S(O)_2NX^{11}X^{12}$, $—NX^6S(O)_2X^{12}$, $—NX^6CONX^{11}X^{12}$, $—NX^6S(O)_2$ $NX^{11}X^{12}$, $—NX^6C(O)X^{12}$, imidazolyl, thiazolyl and tetrazolyl, provided that if $A^1$ is optionally substituted with methylenedioxy then it can only be substituted with one methylenedioxy;

where $X^{11}$ is hydrogen or optionally substituted $(C_1-C_6)$alkyl;

the optionally substituted $(C_1-C_6)$alkyl defined for $X^{11}$ is optionally independently substituted with phenyl, phenoxy, $(C_1-C_6)$alkoxycarbonyl, $-S(O)_m(C_1-C_6)$alkyl, 1 to 5 halo groups, 1 to 3 hydroxy groups, 1 to 3 $(C_1-C_{10})$ alkanoyloxy groups or 1 to 3 $(C_1-C_6)$alkoxy groups;

$X^{12}$ is hydrogen, $(C_1-C_6)$alkyl, phenyl, thiazolyl, imidazolyl, furyl or thienyl, provided that when $X^{12}$ is not hydrogen, the $X^{12}$ group is optionally substituted with one to three substituents independently selected from the group consisting of Cl, F, $CH_3$, $OCH_3$, $OCF_3$ and $CF_3$;

or $X^{11}$ and $X^{12}$ are taken together to form $-(CH_2)_r-L^1-(CH_2)_r-$;

$L^1$ is $C(X^2)(X^2)$, O, $S(O)_m$ or $N(X^2)$;

$X^6$ for each occurrence is independently hydrogen, optionally substituted $(C_1-C_6)$alkyl, $(C_2-C_6)$ halogenated alkyl, optionally substituted $(C_3-C_7)$ cycloalkyl, $(C_3-C_7)$-halogenated cycloalkyl, where optionally substituted $(C_1-C_6)$alkyl and optionally substituted $(C_3-C_7)$cycloalkyl in the definition of $X^6$ is optionally independently mono- or di-substituted with $(C_1-C_4)$alkyl, hydroxy, $(C_1-C_4)$alkoxy, carboxyl, $CONH_2$, $-S(O)_m(C_1-C_6)$alkyl, carboxylate $(C_1-C_4)$ alkyl ester or 1H-tetrazol-5-yl; or when there are two $X^6$ groups on one atom and both $X^6$ are independently $(C_1-C_6)$alkyl, the two $(C_1-C_6)$alkyl groups may be optionally joined and, together with the atom to which the two $X^6$ groups are attached, form a 4- to 9-membered ring optionally having oxygen, sulfur or $NX^7$ as a ring member;

r for each occurrence is independently 1, 2 or 3;

$X^2$ for each occurrence is independently hydrogen, optionally substituted $(C_1-C_6)$alkyl or optionally substituted $(C_3-C_7)$cycloalkyl, where the optionally substituted $(C_1-C_6)$alkyl and optionally substituted $(C_3-C_7)$cycloalkyl in the definition of $X^2$ are optionally independently substituted with $-S(O)_m(C_1-C_6)$alkyl, $-C(O)OX^3$, 1 to 5 halo groups or 1-3 $OX^3$ groups;

$X^3$ for each occurrence is independently hydrogen or $(C_1-C_6)$alkyl;

$X^7$ is hydrogen or $(C_1-C_6)$alkyl optionally substituted with hydroxy;

m for each occurrence is independently 0, 1 or 2;

provided that $X^6$ and $X^{12}$ cannot be hydrogen when attached to C(O) or $S(O)_2$ in the form $C(O)X^6$, $C(O)X^{12}$, $S(O)_2X^6$ or $S(O)_2X^{12}$; and Pt is an amine protecting group;

comprising reacting a compound of Formula III,

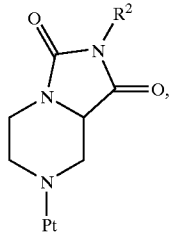

III wherein Pt and $R^2$ are as defined hereinabove, with an alkylating agent of formula $R^1-Z$, wherein $R^1$ is as defined hereinabove and Z is a leaving group, in the presence of a suitable base and a reaction inert solvent.

A preferred process within Process F, designated Process G, comprises the process wherein $R^1$ is $-(CH^2)_q-A^1$ or $(C_1-C_7)$alkyl; and $R^2$ is hydrogen, $(C_1-C_8)$alkyl or $-(C_0-C_3)$alkyl-$(C_3-C_8)$cycloalkyl; where the alkyl groups and the cycloalkyl groups in the definition of $R^2$ are optionally substituted with 1, 2 or 3 fluorine and wherein Pt is tert-butyloxycarbonyl.

A preferred process within Process G, designated Process H, comprises the process wherein Z in said alkylating agent is p-toluenesulfonyloxy, methanesulfonyloxy or halo; said base is alkaline metal bis(trimethylsilyl)amide or alkaline alkoxide; and said reaction inert solvent is N,N-dimethylformamide, tetrahydrofuran, toluene, isopropyl ether, MTBE or a mixture thereof.

A preferred process within Process H, designated Process I, comprises the process wherein $R^1$ is $-CH_2-A^1$, Z is Cl, Br or I, $R^2$ is hydrogen or $(C_1-C_3)$alkyl optionally substituted with 1, 2 or 3 fluoro groups.

A preferred process within Process I, designated Process J, comprises the process wherein $A^1$ is phenyl, pyridyl or thiazolyl, optionally substituted with one to three substituents, each substituent being independently selected from the group consisting of F, Cl, $CH_3$, $OCF_2H$, $OCF_3$ and $CF_3$; and $R^2$ is methyl, ethyl or 2,2,2-trifluoroethyl.

An especially preferred process within Process J is the process wherein $R^1$ is pyridin-2-ylmethyl or benzyl, where said benzyl is optionally substituted with up to two fluoro, chloro or trifluoromethyl; and $R^2$ is methyl.

Another especially preferred process within Process J is the process wherein $R^1$ is pyridin-2-ylmethyl or benzyl, where said benzyl is optionally substituted with up to two fluoro, chloro or trifluoromethyl; and $R^2$ is ethyl.

Yet another especially preferred process within Process J is the process wherein $R^1$ is pyridin-2-ylmethyl or benzyl, where said benzyl is optionally substituted with up to two fluoro, chloro or trifluoromethyl; and $R^2$ is 2,2,2-trifluoroethyl.

This invention is also directed to a process, designated Process K, for preparing a compound of Formula V,

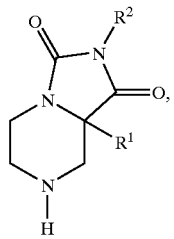

V wherein $R^1$ is $-(CH_2)_qN(X^6)C(O)X^6$, $-(CH_2)_qN(X^6)C(O)(CH_2)_t-A^1$, $-(CH_2)_qN(X^6)S(O)_2(CH_2)_t-A^1$, $-(CH_2)_qN(X^6)S(O)_2X^6$, $-(CH_2)_qN(X^6)C(O)N(X^6)(CH_2)_t-A^1$, $-(CH_2)_qN(X^6)C(O)N(X^6)(X^6)$, $-(CH_2)_qC(O)N(X^6)(X^6)$, $-(CH_2)_qC(O)N(X^6)(CH_2)_t-A^1$, $-(CH^2)_qC(O)OX^6$, $-(CH_2)_qC(O)O(CH_2)_t-A^1$, $-(CH_2)_qOX^6$, $-(CH_2)_qOC(O)X^6$, $-(CH_2)_qOC(O)(CH_2)_t-A^1$, $-(CH_2)_qOC(O)N(X^6)(CH_2)_t-A^1$, $-(CH_2)_qOC(O)N(X^6)(X^6)$, $-(CH_2)_qC(O)X^6$, $-(CH_2)_qC(O)(CH_2)_t-A^1$, $-(CH_2)_qN(X^6)C(O)OX^6$, $-(CH_2)_qN(X^6)S(O)_2N(X^6)(X^6)$, $-(CH_2)_qS(O)_mX^6$, $-(CH_2)_t-A^1$, $-(C_1-C_{10})$alkyl, $-(CH_2)_q-A^1$, $-(CH_2)_q-(C_3-C_7)$cycloalkyl, $-(CH_2)_q-Y^1-(C_1-C_6)$alkyl, $-(CH_2)_q-Y^1-(CH_2)_t-A^1$ or $-(CH_2)_q-Y^1-(CH_2)_t-(C_3-C_7)$cycloalkyl;

where the alkyl and cycloalkyl groups in the definition of $R^1$ are optionally substituted with $(C_1-C_4)$alkyl, hydroxy, $(C_1-C_4)$alkoxy, carboxyl, —$CONH_2$, —$S(O)_m(C_1-C_6)$alkyl, —$CO_2(C_1-C_4)$alkyl ester, 1H-tetrazol-5-yl or 1, 2 or 3 fluoro groups;

$Y^1$ is O, $S(O)_m$, —$C(O)NX^6$—, —CH=CH—, —C≡C—, —$N(X^6)C(O)$—, —$C(O)NX^6$—, —C(O)O—, —OC(O)N(X^6)— or —OC(O)—;

q is 1, 2, 3 or 4;

t is 0, 1, 2 or 3;

said $(CH_2)_q$ group and $(CH_2)_t$ group in the definition of $R^1$ are optionally independently substituted with hydroxy, $(C_1-C_4)$alkoxy, carboxyl, —$CONH_2$, —$S(O)_m(C_1-C_6)$alkyl, —$CO_2(C_1-C_4)$alkyl ester, 1H-tetrazol-5-yl, 1, 2 or 3 fluoro groups or 1 or 2 $(C_1-C_4)$alkyl groups; and $R^2$ is hydrogen, $(C_1-C_8)$alkyl, —$(C_0-C_3)$alkyl-$(C_3-C_8)$ cycloalkyl, —$(C_1-C_4)$alkyl-$A^1$ or $A^1$;

where the alkyl groups and the cycloalkyl groups in the definition of $R^1$ are optionally substituted with hydroxy, —$C(O)OX^6$, —$C(O)N(X^6)(X^6)$, —$N(X^6)(X^6)$, —$S(O)_m(C_1-C_6)$alkyl, —$C(O)A^1$, —$C(O)(X^6)$, $CF_3$, CN or 1, 2 or 3 independently selected halo groups;

$A^1$ for each occurrence is independently selected from the group consisting of $(C_5-C_7)$cycloalkenyl, phenyl, a partially saturated, fully saturated or fully unsaturated 4- to 8-membered ring optionally having 1 to 4 heteroatoms independently selected from the group consisting of oxygen, sulfur and nitrogen and a bicyclic ring system consisting of a partially saturated, fully unsaturated or fully saturated 5- or 6-membered ring, optionally having 1 to 4 heteroatoms independently selected from the group consisting of nitrogen, sulfur and oxygen, fused to a partially saturated, fully saturated or fully unsaturated 5- or 6-membered ring, optionally having 1 to 4 heteroatoms independently selected from the group consisting of nitrogen, sulfur and oxygen;

$A^1$ for each occurrence is independently optionally substituted, on one or optionally both rings if $A^1$ is a bicyclic ring system, with up to three substituents, each substituent independently selected from the group consisting of F, Cl, Br, I, $OCF_3$, $OCF_2H$, $CF_3$, $CH_3$, $OCH_3$, —$OX^6$, —$C(O)N(X^6)(X^6)$, —$C(O)OX^6$, oxo, $(C_1-C_6)$alkyl, nitro, cyano, benzyl, —$S(O)_m(C_1-C_6)$alkyl, 1H-tetrazol-5-yl, phenyl, phenoxy, phenylalkyloxy, halophenyl, methylenedioxy, —$N(X^6)(X^6)$, —$N(X^6)C(O)(X^6)$, —$S(O)_2N(X^6)(X^6)$, —$N(X^6)S(O)_2$-phenyl, —$N(X^6)S(O)_2X^6$, —$CONX^{11}X^{12}$, —$S(O)_2NX^{11}X^{12}$, —$NX^6S(O)_2X^{12}$, —$NX^6CONX^{11}X^{12}$, —$NX^6S(O)_2NX^{11}X^{12}$, —$NX^6C(O)X^{12}$, imidazolyl, thiazolyl and tetrazolyl, provided that if $A^1$ is optionally substituted with methylenedioxy then it can only be substituted with one methylenedioxy;

where $X^{11}$ is hydrogen or optionally substituted $(C_1-C_6)$alkyl;

the optionally substituted $(C_1-C_6)$alkyl defined for $X^{11}$ is optionally independently substituted with phenyl, phenoxy, $(C_1-C_6)$ alkoxycarbonyl, —$S(O)_m(C_1-C_6)$alkyl, 1 to 5 halo groups, 1 to 3 hydroxy groups, 1 to 3 $(C_1-C_{10})$alkanoyloxy groups or 1 to 3 $(C_1-C_6)$ alkoxy groups;

$X^{12}$ is hydrogen, $(C_1-C_6)$alkyl, phenyl, thiazolyl, imidazolyl, furyl or thienyl, provided that when $X^{12}$ is not hydrogen, the $X^{12}$ group is optionally substituted with one to three substituents independently selected from the group consisting of Cl, F, $CH_3$, $OCH_3$, $OCF_3$ and $CF_3$;

or $X^{11}$ and $X^{12}$ are taken together to form —$(CH_2)_r$—$L^1$—$(CH_2)_r$—;

$L^1$ is $C(X^2)(X^2)$, O, $S(O)_m$ or $N(X^2)$;

$X^6$ for each occurrence is independently hydrogen, optionally substituted $(C_1-C_6)$alkyl, $(C_2-C_6)$ halogenated alkyl, optionally substituted $(C_3-C_7)$ cycloalkyl, $(C_3-C_7)$-halogenated cycloalkyl, where optionally substituted $(C_1-C_6)$alkyl and optionally substituted $(C_3-C_7)$cycloalkyl in the definition of $X^6$ is optionally independently mono- or di-substituted with $(C_1-C_4)$alkyl, hydroxy, $(C_1-C_4)$alkoxy, carboxyl, $CONH_2$, —$S(O)_m(C_1-C_6)$alkyl, carboxylate $(C_1-C_4)$ alkyl ester or 1H-tetrazol-5-yl; or when there are two $X^6$ groups on one atom and both $X^6$ are independently $(C_1-C_6)$alkyl, the two $(C_1-C_6)$alkyl groups may be optionally joined and, together with the atom to which the two $X^6$ groups are attached, form a 4- to 9-membered ring optionally having oxygen, sulfur or $NX^7$ as a ring member;

r for each occurrence is independently 1, 2 or 3;

$X^2$ for each occurrence is independently hydrogen, optionally substituted $(C_1-C_6)$alkyl or optionally substituted $(C_3-C_7)$cycloalkyl, where the optionally substituted $(C_1-C_6)$alkyl and optionally substituted $(C_3-C_7)$cycloalkyl in the definition of $X^2$ are optionally independently substituted with —$S(O)_m(C_1-C_6)$alkyl, —$C(O)OX^3$, 1 to 5 halo groups or 1–3 $OX^3$ groups;

$X^3$ for each occurrence is independently hydrogen or $(C_1-C_6)$alkyl;

$X^7$ is hydrogen or $(C_1-C_6)$alkyl optionally substituted with hydroxy;

m for each occurrence is independently 0, 1 or 2;

provided that $X^6$ and $X^{12}$ cannot be hydrogen when attached to C(O) or $S(O)_2$ in the form $C(O)X^6$, $C(O)X^{12}$, $S(O)_2X^6$ or $S(O)_2X^{12}$;

comprising reacting a compound of Formula I,

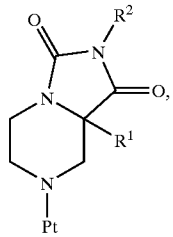

wherein Pt is an amine protecting group and $R^1$ and $R^2$ are as defined hereinabove;

with an acid in the presence of a reaction inert solvent.

A preferred process within Process K, designated Process L, comprises the process wherein $R^1$ is —$(CH_2)_q$—$A^1$ or $(C_1-C_7)$alkyl; and $R^2$ is hydrogen, $(C_1-C_8)$alkyl or —$(C_0-C_3)$alkyl-$(C_3-C_8)$cycloalkyl; where the alkyl groups and the cycloalkyl groups in the definition of $R^2$ are optionally substituted with 1, 2 or 3 fluorine and wherein Pt is t-butyloxycarbonyl.

A preferred process within Process L, designated Process M, comprises the process wherein said acid is methanesulfonic acid, and said reaction inert solvent is methylene chloride.

A preferred process within Process M, designated Process N, comprises the process wherein is $R^1$ is —$CH_2$—$A^1$; and $R^2$ is hydrogen or ($C_1$–$C_3$)alkyl optionally substituted with 1, 2 or 3 fluoro groups.

A preferred process within Process N, designated Process O, comprises the process wherein $R^1$ is —$CH_2$—$A^1$ where $A^1$ is phenyl, pyridyl or thiazolyl, optionally substituted with one to three substituents, each substituent being independently selected from the group consisting of F, Cl, $CH_3$, $OCF_2H$, $OCF_3$ and $CF_3$; and $R^2$ is methyl, ethyl or 2,2,2-trifluoroethyl.

An especially preferred process within Process O comprises the process wherein $R^1$ is pyridin-2-ylmethyl or benzyl, where said benzyl is optionally substituted with up to two fluoro, chloro or trifluoromethyl and particularly where said benzyl is substituted with up to two fluoro; and $R^2$ is methyl. Still more especially preferred within this process is the process wherein $R^1$ is benzyl and $R^2$ is methyl or where $R^1$ is pyridin-2-ylmethyl and $R^2$ is methyl.

Another especially preferred process within Process O comprises the process wherein $R^1$ is pyridin-2-ylmethyl or benzyl, where said benzyl is optionally substituted with up to two fluoro, chloro or trifluoromethyl; and $R^2$ is ethyl. Still more especially preferred within this process is the process wherein $R^1$ is benzyl and $R^2$ is ethyl or where $R^1$ is pyridin-2-ylmethyl and $R^2$ is ethyl.

Yet another especially preferred process within Process O comprises the process wherein $R^1$ is pyridin-2-ylmethyl or benzyl, where said benzyl is optionally substituted with up to two fluoro, chloro or trifluoromethyl; and $R^2$ is 2,2,2-trifluoroethyl. Still more especially preferred within this process is the process wherein $R^1$ is benzyl and $R^2$ is trifluoroethyl or where $R^1$ is pyridin-2-ylmethyl and $R^2$ is trifluoroethyl.

This invention is also directed to a process, designated Process P, for preparing a compound of Formula XIII,

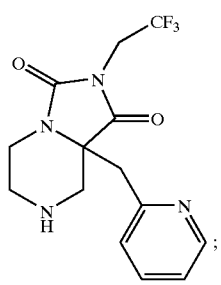

XIII comprising:
(a) reacting piperazine-1,3-dicarboxic acid 1-tert-butyl ester 3-($C_1$–$C_4$)alkyl ester with a carbonyl equivalent and 2,2,2-trifluoroethylamine in the presence of a reaction inert solvent to form the compound of Formula XIV,

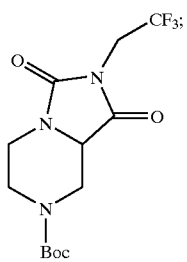

XIV (b) reacting said compound of Formula XIV with 2-picolyl-$Z^1$, wherein $Z^1$ is halo, methanesulfonyloxy or p-toluenesulfonyloxy, in the presence of a base and a reaction inert solvent to form the compound of Formula XV,

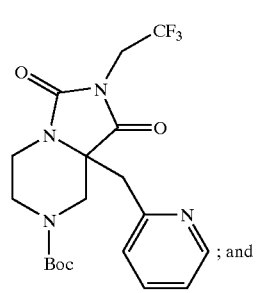

XV

; and (c) reacting said compound of Formula XV with an acid in the presence a reaction inert solvent.

A preferred process within Process P, designated Process Q, comprises the process wherein in step (a), said carbonyl equivalent is N,N'-carbonyldiimidazole, phosgene, diphosgene or triphosgene and said reaction inert solvent is methylene chloride; in step (b), said alkylating agent is 2-picolyl chloride, said base is potassium bis(trimethylsilyl)amide, sodium bis(trimethylsilyl)amide, sodium amide, potassium amide, sodium ($C_1$–$C_4$)alkoxide or potassium ($C_1$–$C_4$) alkoxide and said reaction inert solvent is a mixture of tetrahydrofuran and N,N-dimethylformamide; and in step (c), said acid is methanesulfonic acid and said reaction inert solvent is, methylene chloride.

A preferred process within Process Q is the process wherein in step (a), said carbonyl equivalent is N,N'-carbonyldiimidazole; and in step (b), said base is potassium bis(trimethylsilyl)amide.

This invention is also directed to a process, designated Process R, for preparing a compound of Formula VI,

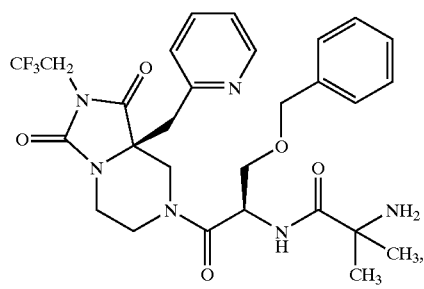

VI comprising
(a) reacting a compound of Formula IV,

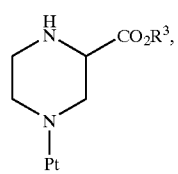

IV wherein Pt is an amine protecting group and $R^3$ is ($C_1$–$C_4$)alkyl,
with a carbonyl equivalent and $CF_3CH_2NH_2$ in a reaction inert solvent to form a compound of Formula VII,

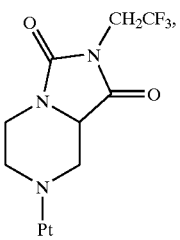

VII wherein Pt is as defined hereinabove;

(b) reacting said compound of Formula VII with 2-picolyl-$Z^1$, wherein $Z^1$ is halo, methanesulfonyloxy or p-toluenesulfonyloxy, in the presence of a base and a reaction inert solvent at a temperature from about −78° C. to about 25° C. for from about one hour to about 24 hours to form a compound of Formula VIII,

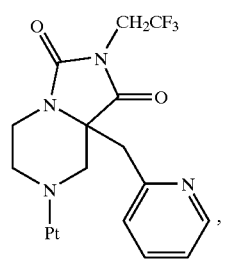

VIII wherein Pt is as defined above;

(c) reacting said compound of Formula VIII with a suitable acid in a reaction inert solvent at a temperature from about −30° C. to about 25° C. for from about one hour to about 10 hours to form a compound of Formula IX,

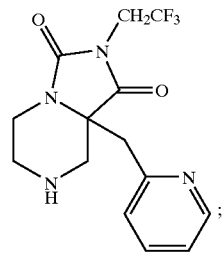

IX (d) resolving said compound of Formula IX with D-tartaric acid in a reaction inert solvent to form the D-tartrate salt of a compound of Formula X,

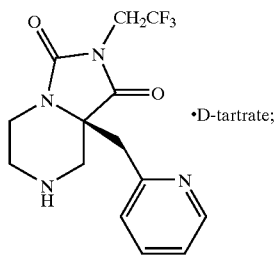

X (e) reacting said D-tartrate salt of a compound of Formula X with a compound of Formula XI,

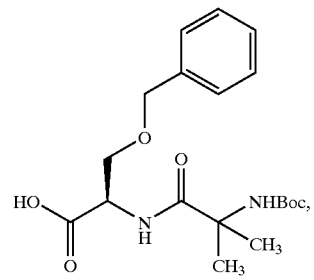

XI wherein Boc is tert-butyloxycarbonyl, a peptide coupling reagent and a base in a reaction inert solvent to form a compound of Formula XII,

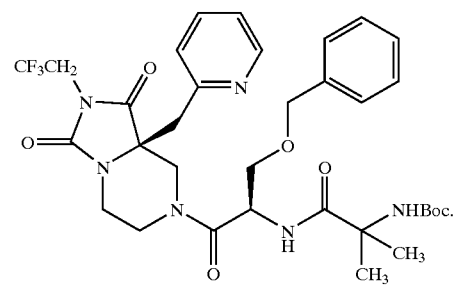

XII (f) reacting said compound of Formula XII under standard t-butyloxycarbonyl group removing conditions to form a compound of Formula VI,

VI

A preferred process within Process R, designated Process S, is the process wherein:
  in step (a), said carbonyl equivalent is N,N'-carbonyldiimidazole, phosgene, diphosgene or triphosgene;
  in step (b), said base is potassium bis(trimethylsilyl)amide, sodium bis(trimethylsilyl)amide, sodium amide, potassium amide, sodium ($C_1$–$C_4$)alkoxide or potassium ($C_1$–$C_4$)alkoxide and
  in step (e), said peptide coupling reagent is EEDQ, EDC, DCC or 1-propanephosphonic acid cyclic anhydride;
A preferred process within Process S, designated Process T, is the process wherein:
  in step (a), said carbonyl equivalent is N,N'-carbonyldiimidazole and said reaction inert solvent is methylene chloride;
  in step (b), said base is potassium bis(trimethylsilyl)amide, sodium bis(trimethylsilyl)amide and said reaction inert solvent is N,N-dimethylformamide, toluene, tetrahydrofuran or a mixture thereof;

in step (c), said acid is methanesulfonic acid and said reaction inert solvent is methylene chloride;

in step (d), said reaction inert solvent is a mixture of acetone and water;

in step (e), said peptide coupling reagent is 1-propanephosphonic acid cyclic anhydride, said base is triethylamine and said reaction inert solvent is ethyl acetate; and in step (f), said standard t-butyloxycarbonyl group removing conditions comprise using hydrochloric acid in methanol.

This invention is particularly directed to a process of Process T wherein 2-amino-N-{1(R)-benzyloxymethyl-2-[1,3-dioxo-8a(S)-pyridin-2-ylmethyl-2-(2,2,2-trifluoro-ethyl)-hexahydro-imidazo[1,5-a]pyrazin-7-yl]-2-oxo-ethyl}-2-methyl-propionamide is prepared.

DETAILED DESCRIPTION OF THE INVENTION

The preparation of the intermediates of Formula I of this invention can be readily carried out as set forth below. The processes of this invention, e.g., to prepare the compounds of Formulas I, II and VI are also set forth in detail below.

In the structural formulas disclosed throughout the instant specification and claims, the following terms have the indicated meanings unless expressly stated otherwise:

The alkyl groups are intended to include those alkyl groups of the designated length in either a straight or branched configuration which may optionally contain one or more double or triple bonds. Exemplary of such alkyl groups are methyl, ethyl, propyl, isopropyl, butyl, sec-butyl, tertiary butyl, pentyl, isopentyl, hexyl, isohexyl, allyl, ethynyl, propenyl, butadienyl, hexenyl and the like.

When the definition $C_0$-alkyl occurs in the definition, it means a single covalent bond.

The alkoxy groups specified above are intended to include those alkoxy groups of the designated length in either a straight or branched configuration which may optionally contain one or more double or triple bonds. Exemplary of such alkoxy groups are methoxy, ethoxy, propoxy, isopropoxy, butoxy, isobutoxy, tertiary butoxy, pentoxy, isopentoxy, hexoxy, isohexoxy, allyloxy, 2-propynyloxy, isobutenyloxy, hexenyloxy and the like.

The term "halogen" or "halo" is intended to include the halogen atoms fluorine (F), chlorine (Cl), bromine (Br) and iodine (I).

The term "halogenated alkyl" is intended to include an alkyl group as defined above substituted by one or more halogen atoms as defined above.

The term "halogenated cycloalkyl" is intended to include a cycloalkyl group substituted by one or more halogen atoms as defined above.

The term "aryl" is intended to include phenyl, naphthyl, aromatic 5-membered rings with one to four heteroatoms, aromatic 6-membered rings with one to four heteroatoms and fused 5- and/or 6-membered bicyclic rings with one to four heteroatoms of nitrogen, sulfur or oxygen. Examples of such heterocyclic aromatic rings are pyridine, thiophene, furan, benzothiophene, tetrazole, indole, N-methylindole, dihydroindole, indazole, N-formylindole, benzimidazole, thiazole, pyrimidine, and thiadiazole.

The term "carbonyl equivalent" means a compound containing two leaving groups attached directly to a carbonyl moiety. When a carbonyl equivalent is reacted with two nucleophiles, said nucleophiles displace both leaving groups resulting in the insertion of a carbonyl group between the two nucleophiles. Preferred carbonyl equivalents include carbonyldiimidazole, phosgene, diphosgene and triphosgene. A particularly preferred carbonyl equivalent is carbonyldiimidazole.

The term "preformed isocyanate" means an isocyanate which is used as a reagent as opposed to an isocyanate which is formed in situ. An example of a preformed isocyanate is methyl isocyanate.

In this specification the following abbreviations are used with the following meanings:

| Boc | t-Butyloxycarbonyl |
|---|---|
| CBZ | Benzyloxycarbonyl |
| CDI | N,N'-Carbonyldiimidazole |
| DCC | Dicyclohexylcarbodiimide |
| DMF | N,N-dimethylformamide |
| EEDQ | 2-Ethoxy-1-ethoxycarbonyl-1,2-dihydroquinoline |
| EDC | 1-(3-Dimethylaminopropyl)-3-ethylcarbodiimide hydrochloride |
| EtOAc | Ethyl acetate |
| FMOC | 9-Fluorenylmethoxycarbonyl |
| Hex | Hexane |
| HPLC | High pressure liquid chromatography |
| Hz | Hertz |
| KHMDS | Potassium Bis(trimethylsilyl)amide |
| MHz | Megahertz |
| MS | Mass Spectrum |
| MTBE | tert-Butyl methyl ether |
| NMR | Nuclear Magnetic Resonance |
| PPAA | 1-Propanephosphonic acid cyclic anhydride |
| THF | Tetrahydrofuran |

Certain of the above defined terms may occur more than once in the varioius structural formulas set forth herein. Upon each occurrence such terms shall be defined independently of any others.

General Synthesis

The process of the instant invention is readily carried out as described below.

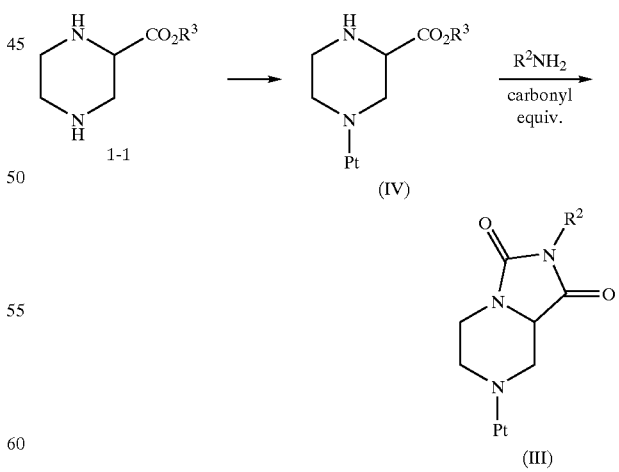

According to Scheme 1, the compounds of Formula III wherein Pt is an amine protecting group and $R^2$ is as defined above may be prepared from piperazine-2-carboxylate esters of formula 1-1 wherein $R^3$ is $(C_1-C_4)$alkyl. For example, ethyl piperazine-2-carboxylate is protected under standard conditions well known to those skilled in the art with a suitable amine protecting group to afford the compound of Formula IV wherein $R^3$ is ethyl, which is reacted with a preformed isocyanate or an amine of formula $R^2$—$NH_2$ and a carbonyl equivalent such as carbonyldiimidazole, phosgene, diphosgene or triphosgene to afford the compound of Formula III.

Any amine protecting group known to those skilled in the art of peptide chemistry can be utilized according to Scheme 1 to protect the 4-position of the piperazine ring. Among the protecting groups, Boc is preferably used for its stability to subsequent reaction conditions. For example, protection of the 4-amino group of ethyl piperazine-2-carboxylate with Boc can be carried out according to procedures well known to those skilled in the art. For example, ethyl piperazine-2-carboxylate is reacted with di-tert-butyl dicarbonate in the presence of a base such as triethylamine, 4-dimethylaminopyridine, diisopropylethylamine, potassium hydroxide or sodium hydroxide. This reaction can be carried out at a temperature from about 0° C. to about 80° C. for from about one hour to about 24 hours. Preferably protection of the amine is carried out at 0° C. in methylene chloride.

The compound of Formula IV is reacted with an amine of formula $R^2$—$NH_2$ and a carbonyl equivalent in the presence of a suitable tertiary amine in a reaction inert solvent at a temperature from about 0° C. to about 80° C. for from about one hour to about 72 hours. A suitable reaction inert solvent is methylene chloride. Suitable carbonyl equivalents include carbonyldiimidazole, phosgene, diphosgene and triphosgene. Carbonyl diimidazole is particularly preferred. Suitable tertiary amines include triethylamine and diisopropylethylamine. Triethylamine is particularly preferred. The compound of Formula IV may also be reacted with an isocyanate, such as methyl isocyanate in a reaction inert solvent at from about room temperature to about 60° C. A suitable solvent is refluxing acetone.

defined above and Z is a suitable leaving group in the presence of a suitable base to give the compound of Formula I. Suitable leaving groups include methanesulfonyloxy, p-toluenesulfonyloxy and halo. In a particularly preferred pathway, $R^1$—Z is 2-picolyl chloride. Suitable bases include alkaline amides and alkaline $(C_1–C_4)$alkoxides such as sodium ethoxide, sodium methoxide, potassium t-butoxide, lithium bis(trimethylsilyl)amide, sodium bis(trimethylsilyl)amide or potassium bis(trimethylsilyl)amide. The alkylation reaction is carried out in a reaction inert solvent such as N,N-dimethylformamide, tetrahydrofuran, diethyl ether, toluene and the like. The reaction is carried out at about −78° C. to about 25° for about one hour to about 24 hours. When the alkylating agent contains a ring nitrogen atom, such as 2-picolyl chloride, it is preferred to use the free base form of the alkylating agent.

After alkylation is complete, the amine protecting group (Pt) of the compound of Formula I is removed by performing deprotection procedures well known to those skilled in the art. When Pt is CBZ, for example, the CBZ group is removed by hydrogenation over a catalyst. An acid such as hydrochloric acid or trifluoroacetic acid may be added to the hydrogenation mixture to ensure complete reaction. It is preferred that a palladium catalyst is used in the removal of CBZ groups.

Alternatively, when Pt is Boc, which is the preferred protecting group, the skilled person may treat the compound of Formula I with an acid to effect deprotection. Preferred acids for such deprotections include trifluoroacetic acid, methanesulfonic acid and dilute hydrochloric acid. It is particularly preferred to deprotect the instant Boc-protected amine by treating the compound of Formula III with methanesulfonic acid in a polar solvent such as methanol, ethanol and dichloromethane at a temperature from about −30° C. to about 25° C. for about one hour to about 24 hours.

The compounds of Formula V thus prepared are obtained in racemic form. Optical resolution of the compounds of Formula V can be carried out to afford compounds of Formula X according to the procedures set forth in Scheme 3.

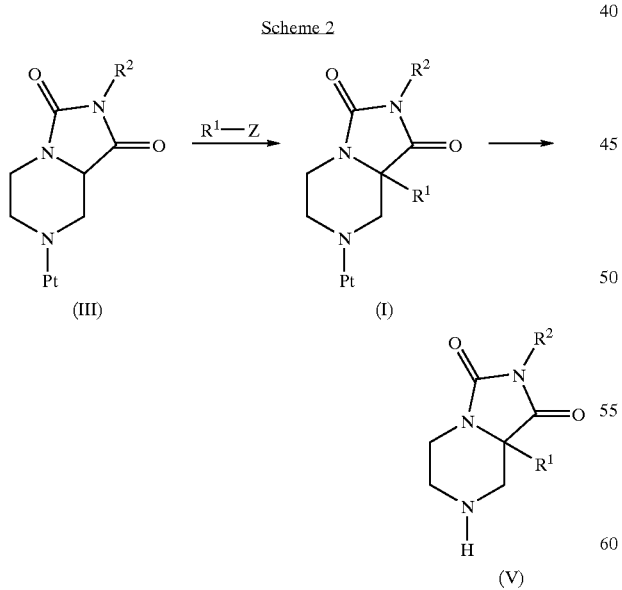

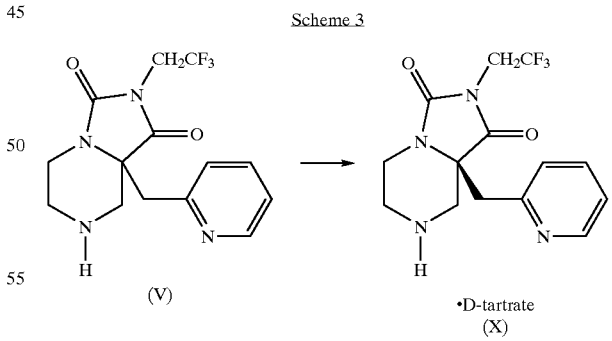

According to Scheme 2, the intermediate compounds of Formula I are prepared from compounds of Formula III. For example, a compound of Formula III is reacted with an alkylating agent of the formula $R^1$—Z wherein $R^1$ is as According to Scheme 3, a compound of Formula V is resolved into its separate optically active enantiomer of Formula X by treating a compound of Formula V with D-tartaric acid in a suitable mixed solvent system comprising a polar organic solvent and water (e.g., ketone/water such as acetone/water or alcohol/water such as methanol/water). The resulting diastereomers are separated by methods well known to those skilled in the art.

Scheme 4

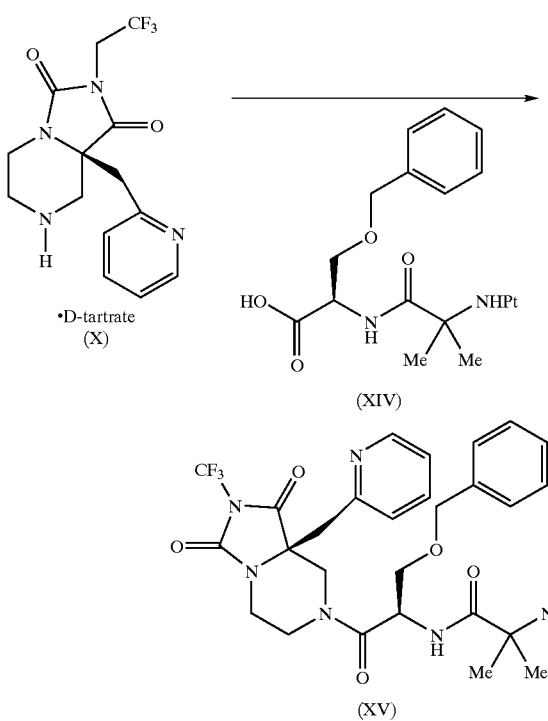

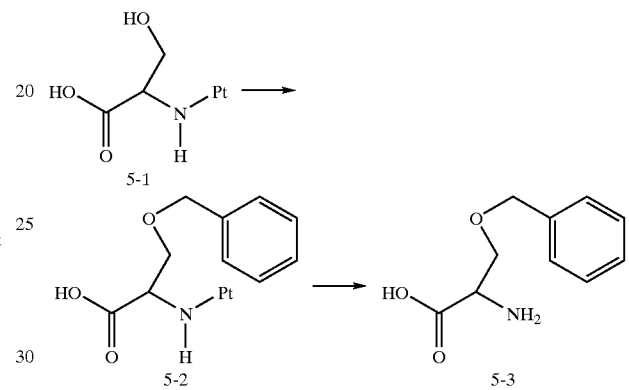

According to Scheme 4, a compound of Formula X is condensed with a compound of Formula XIV to yield a compound of Formula XV. This condensation is performed in the presence of a suitable peptide coupling reagent such as EEDQ, EDC, DCC or PPAA and a base such as triethylamine or diisopropylethylamine in a reaction inert solvent at a temperature of about −55° C. to about 0° C. for about one half hour to about eight hours. Preferred reaction inert solvents include ethyl acetate, tetrahydrofuran and methylene chloride. Ethyl acetate is particularly preferred. PPAA is a particularly preferred peptide coupling reagent. A particularly preferred base is triethylamine. Typically, the protecting group (P) on the compound of Formula XIV is Boc, which is removed as set forth above or according to other procedures well known to those skilled in the art such as those procedures set forth in Protecting Groups in Organic Synthesis, Greene and Wuts, Eds., (John Wiley & Sons, New York, 1991).

The compound of Formula X can be used in its free-base in this condensation. The free-base form of the compound of Formula X can be formed by treating a compound of Formula X with ammonium hydroxide or aqueous sodium bicarbonate.

Scheme 5

As illustrated in Scheme 5, an intermediate ether of formula 5-2 can be prepared by treating an amino acid of formula 5-1, where Pt is a suitable protecting group, with a base such as potassium carbonate or sodium hydride followed by benzyl mesylate, benzyl tosylate or a benzyl halide, such as benzylbromide, in a suitable solvent such as DMF or THF. Deprotection of the amine transforms 5-2 into 5-3.

Scheme 6

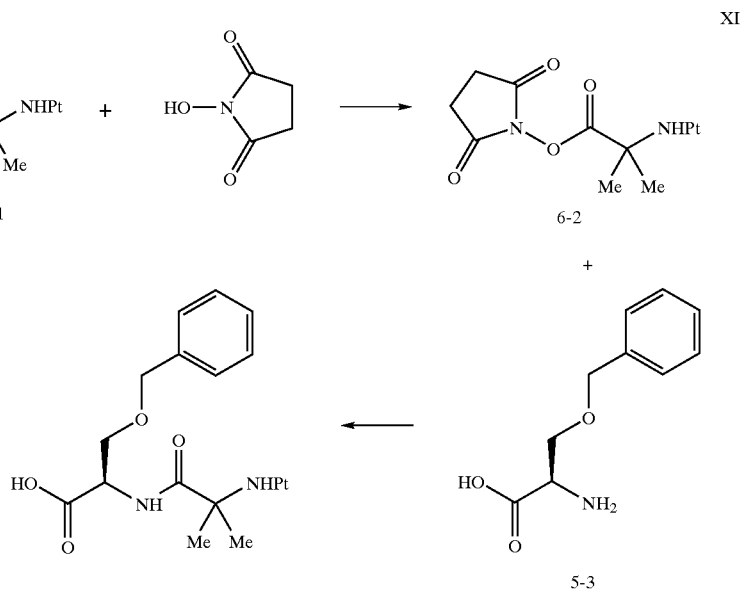

As illustrated in Scheme 6, intermediates of formula 6-2 can be prepared by treating an acid of formula 6-1 with hydroxysuccinimide in the presence of a coupling agent such as EDC in an inert solvent such as methylene chloride. Treating 6-2 with an amino acid of formula 5-3 at about room temperature in a solvent such as DMF in the presence of a base such as diisopropylethylamine or triethylamine produces compounds of formula XI.

($C_1$–$C_4$)Alkyl piperazine-2-carboxylates can be synthesized according to procedures well known to those skilled in the art such as the procedure set forth in Synthesis, 1992, 1065–1066. For example, ethyl piperazine-2-carboxylate can be prepared by coupling ethyl 2,3-dibromopropionate and N,N'-dibenzylethylene diamine according to known alkylation methods. This reaction is typically performed in the presence of a base such as triethylamine in a reaction inert solvent at a temperature from about 25° C. to about 100° C. for about one hour to about 24 hours, preferably under nitrogen. A particularly preferred solvent for this reaction is toluene. The N-benzyl groups can be removed by hydrogenation to afford alkyl piperazine-2-carboxylates.

Alternatively, ($C_1$–$C_4$)alkyl piperazine-2-carboxylates can be prepared by esterification of piperazine-2-carboxylic acid with ethanol in the presence of a suitable acid catalyst such as sulfuric acid, hydrogen chloride or p-toluenesulfonic acid results in the formation of ethyl piperazine-2-carboxylate (e.g., M. D. Armstrong et al., J. Am. Chem. Soc., 77:6049–6051; (1955)).

The compounds of Formula II prepared by the processes of the instant invention all have at least two asymmetric centers as noted by the wedge-shaped bonds in the structural formula. Additional asymmetric centers may be present on the molecule depending upon the nature of the various substituents on the molecule. Each such asymmetric center will produce two optical isomers and it is intended that all such optical isomers, as separated, pure of partially purified optical isomers, racemic mixtures or diastereomeric mixtures thereof, be included in the compounds represented by Formula II.

The compounds of Formula II and VI prepared by the processes of this invention are generally isolated in the form of their pharmaceutically acceptable acid addition salts, such as the salts derived from using inorganic and organic acids. Examples of such acids are hydrochloric, nitric, sulfuric, phosphoric, formic, acetic, trifluoroacetic, propionic, maleic, succinic, D-tartaric, L-tartaric, malonic, methane sulfonic and the like. In addition, certain compounds containing an acidic function such as a carboxy can be isolated in the form of their inorganic salt in which the counter-ion can be selected from sodium, potassium, lithium, calcium, magnesium and the like, as well as from organic bases.

The pharmaceutically acceptable salts are formed by taking about 1 equivalent of a compound of Formula II and contacting it with about 1 equivalent of the appropriate corresponding acid of the salt which is desired. Work-up and isolation of the resulting salt is well-known to those of ordinary skill in the art.

As disclosed in commonly assigned International Application Number PCT/IB98/00873, the growth hormone secretagogues of Formula II prepared by the processes of this invention are useful in vitro as unique tools for understanding how growth hormone secretion is regulated at the pituitary level. As such the compounds of Formula II are useful for all of the utilities set forth therein and may be administered as set forth therein. Further, dosages of the compounds of Formula II may be determined as set forth therein.

Many protected amino acid derivatives are commercially available, where the amine protecting groups are, for example, Boc, CBZ, FMOC, benzyl or ethoxycarbonyl groups. Other protected amino acid derivatives can be prepared by literature methods well-known to one skilled in the art. Some substituted piperazines and piperidines are commercially available, and many other piperazines and 4-substituted piperidines are known in the literature. Various heterocyclic substituted piperidines and piperazines can be prepared following literature methods using derivatized heterocyclic intermediates. Alternatively,the heterocyclic rings of such compounds can be derivatized by standard means, such as coupling with CDl, hydrogenation of aromatic heterocycles, etc. as is well-known to those skilled in the art.

Many of the reactions of this invention concern compounds which contain amine protecting groups (Pt), which can be any suitable protecting group known to those skilled in the art. Benzyloxycarbonyl groups can be removed by a number of methods including, catalytic hydrogenation with hydrogen in the presence of a palladium or platinum catalyst in a protic solvent such as methanol. Preferred catalysts are palladium hydroxide on carbon or palladium on carbon. Hydrogen pressures from 1–1000 psi can be employed; pressures from 10 to 70 psi are preferred. Alternatively, the benzyloxycarbonyl group can be removed by transfer hydrogenation.

Removal of Boc protecting groups can be carried out using a strong acid such as trifluoroacetic acid, methanesulfonic acid or hydrochloric acid with or without the presence of a cosolvent such as dichloromethane or methanol at a temperature of about −30° C. to about 70° C., preferably about −5° C. to about 35° C.

Benzyl groups on amines can be removed by a number of methods including catalytic hydrogenation with hydrogen in the presence of a palladium catalyst in a protic solvent such as methanol. Hydrogen pressures from 1–1000 psi can be employed; pressures from 10 to 70 psi are preferred. The addition and removal of these and other protecting groups are discussed in detail by T. Greene in Protective Groups in Organic Synthesis, John Wiley & Sons, New York, 1981. General Procedure A: (Cleavage of a Boc-protecting group from a Boc-protected amine using concentrated HCl): The Boc-protected amine is dissolved in a minimum volume of ethanol and the resulting solution is cooled to about 0° C. and concentrated HCl (typically about 1 to 4 mL per mmol of Boc-procted amine) is added and the reaction mixture is warmed to room temperature and stirred for about one hour to about 2.5 hours (or the time required for complete disappearance of the starting material to a more polar product as judged by thin layer chromatography). The resulting solution or suspension is concentrated and the residue is coevaporated several times with added ethanol to afford the amine hydrochloride which is used without further purification or purified as specified.

EXAMPLE 1

Step 1: Ethyl 1,4-dibenzylpiperazine-2-carboxylate

To a stirred solution of ethyl 2,3-dibromopropionate (142.7 g, 0.549 mol) in dry toluene (2000 mL) was added N,N'-dibenzylethylene diamine (132 g, 0.549 mol), followed by triethylamine (110.8 g, 1.098 mol), under $N_2$ at 40° C. (a dense white precipitate formed immediately, thus good stirring was necessary). The mixture was heated at 80° C. overnight, cooled and filtered. The filtrate was then washed with $H_2O$, dried over $MgSO_4$, and concentrated under reduced pressure. The residue oil was taken on to the next step without further purification (GC-MS shows one peak at 6.79) or purified by column chromatography (EtOAc/hexane 1:4). Weight of crude product: 169.6 g (91%).

Any impurities present in product are removed upon granulation in the following step.

Step 2: Ethyl piperazine-2-carboxylate

Procedure A: Ethyl 1,4-dibenzylpiperazine-2-carboxylate (prepared as described in Step 1, 33.8 g, 0.1 mol) was dissolved in ethanol (500 mL) and hydrogenated over 10% Pd-C (10 g) at room temperature and 50 psi pressure in the presence of 10 equivalents of acetic acid (60 g) overnight. The mixture was filtered through a pad of Celite® to remove the catalyst. The catalyst was washed with ethanol. The filtrate/washings were combined and concentrated to give a yellow syrup. To the yellow syrup was added 50 mL of EtOAc and 50 mL of hexanes. The suspension was stirred at room temperature for 1 h and the resulting white solid was collected by filtration to afford 24 g (88%) of the title compound.

Procedure B: To a stirred solution of ethyl 1,4-dibenzylpiperazine-2-carboxylate (prepared as described in Step 1, 6.929 g, 20.5 mmol) in dry methanol (120 mL) under $N_2$ was added 10% Pd/C (6.0 g) and anhydrous ammonium formate (10.25 g, 162.5 mmol). The resulting mixture was refluxed under $N_2$ for 3 h. The mixture was filtered through a pad of Celites to remove the catalyst. The catalyst was washed with methanol. The filtrate was concentrated to give a yellow syrup, To the yellow syrup was added 3 mL of AcOH in 20 mL of EtOAc/20 mL of hexanes. The white solid which precipitated upon stirring was collected by filtration to afford 4.85 g (86%) of the title compound. cl Step 3: Piperazine-1,3-dicarboxylic acid 1-tert-butyl ester 3-ethyl ester A solution of di-tert-butyl-dicarbonate (40.72 g, 0.186 mol) in $CH_2Cl_2$ (250 mL) was added slowly to a mixture of ethyl piperazine-2-carboxylate (prepared according to the method described in Step 2, 48.69 g, 0.178 mol) and triethylamine (89.74 g, 0.889 mol) in $CH_2Cl_2$ (600 mL) at 0° C. with good stirring. The mixture was stirred overnight. The reaction mixture was then washed with $H_2O$, dried over $MgSO_4$ and concentrated to give 43.22 g of crude product (94%). The product was taken on to the next step without any purification.

Step 4: 1,3-Dioxo-2-(2,2,2-trifluoro-ethyl)-hexahydro-imidazo[1,5-a]pyrazine-7-carboxylic acid tert-butyl ester Triethylamine (47.60 g, 0.47 mol) was added to a suspension of N,N'-carbonyldiimidazole (65.38 g, 0.403 mol) and 2,2,2-trifluoroethylamine HCl (63.75 g, 0.47 mol) in $CH_2Cl_2$ (800 mL). The mixture was stirred over the weekend. To the solution was added piperazine-1,3-dicarboxylic acid 1-tert-butyl ester 3-ethyl ester (prepared as described in Step 3, 43.22 g, 0.168 mol) in $CH_2Cl_2$ (350 mL) and the resulting solution was stirred at room temperature for 2 days. The solution was diluted with 250 mL of $H_2O$ and extracted with $CH_2Cl_2$ (3×350 mL). The product was purified by granulation in hexane to afford 57.80 g (100%) of the title compound.

Step 5: 1,3-Dioxo-8a-pyridin-2-ylmethyl-2-(2,2,2-trifluoro-ethyl)-hexahydroimidazo [1,5-a]pyrazine-7-carboxylic acid tert-butyl ester In flame-dried glassware, 1,3-dioxo-2-(2,2,2-trifluoro-ethyl)-hexahydro-imidazo[1,5-a]pyrazine-7-carboxylic acid tert-butyl ester (prepared as described in Step 4, 10.11 g, 30 mmol) was dissolved in 150 mL of DMF/30 mL of THF and cooled to −78° C. Potassium bis(trimethylsilyl)amide (KHMDS, 0.5 M solution, 90 mL, 45 mmol) was added dropwise and allowed to stir for 1 h at −78° C. In separate glassware, 2-picolyl chloride HCl (14.76 g, 90 mmol) was reacted with saturated aqueous $NaHCO_3$ (150 mL), extracted with $CH_2Cl_2$ (3×150 mL), dried with $MgSO_4$, evaporated and added 50 mL of dry THF with some molecular sieves. The resulting solution of 2-picolyl chloride free base was added to the reaction mixture at −78° C. via syringe and allowed to warm to room temperature overnight. The toluene and THF were evaporated and resulting DMF solution was partitioned with 150 mL of $H_2O$/150 mL of IPE. 1,4-Diazabicyclo[2,2,2]octane (7.3 g, 65 mmol) and $K_2CO_3$ (12 g, 90 mmol) were added to the solution and the solution was stirred for one hour to remove excess 2-picolyl chloride. The organic solvents were separated and were removed by evaporation to give 11.45 g (89%) of essentially pure title compound.

Step 6: 8a-Pyridin-2-ylmethyl-2-(2,2,2-trifluoro-ethyl)-tetrahydro-imidazo[1,5-a]pyrazine-1,3-dione To a solution of 1,3-dioxo-8a-pyridin-2-ylmethyl-2-(2,2,2-trifluoro-ethyl)-hexahydro-imidazo[1,5-a]pyrazine-7-carboxylic acid tert-butyl ester (prepared as described in Step 5, 1.89 g, 4.4 mmol) in $CH_2Cl_2$ (20 mL) was added $MeSO_3H$ (2.14 g, 22 mmol). The reaction mixture was stirred at room temperature for one hour. Triethylamine (2.45 g, 24.2 mmol) was added to the solution. The organic layer was washed with 100 mL of $H_2O$, brine, dried over $MgSO_4$, and concentrated to give a 1.4 g of the title compound as a yellow oil (97%). The oil solidified upon granulation in hexane or upon cooling.

Step 7: 8a(S)-pyridin-2-ylmethyl-2-(2,2,2-trifluoro-ethyl)-tetrahydro-imidazo[1,5-a]pyrazine-1,3-dione To a solution of 8a-pyridin-2-ylmethyl-2-(2,2,2-trifluoro-ethyl)-tetrahydro-imidazo[1,5-a]pyrazine-1,3-dione (prepared according to the method described in Step 6, 106 g, 0.325 mol) in acetone (2120 mL) and water (212 mL) was added D-tartaric acid (48.46 g, 0.325 mol). White precipitate formed and it was granulated for 3 hours. The solids were collected by suction filtration and washed with acetone. The solvent damp solids were placed in acetone (1000 mL) and stirred at 56° C. overnight. The solids were collected by suction filtration the next morning and dried to give 56 g of the chiral title compound as the D-tartrate salt (73% yield of theory). Chiral HPLC showed an optical purity of 98:2.

The tartrate salt was free-based by stirring with saturated $NaHCO_3$ in EtOAc, and the yield was 96%.

Step 8: (1-(1(R)-Benzyloxymethyl-2-(1,3-dioxo-8a(S)-pyridin-2-ylmethyl-2(2,2,2-trifluoro-ethyl)-hexahydro-imidazo[1,5-a]pyrazin-7-yl)-2-oxo-ethylcarbamoyl)-1-methyl-ethyl-carbamic acid tert-butyl ester To a solution of the title compound of Step 7 (10.0 g, 30.5 mmol) and the title compound of Preparation Two (13.9 g, 36.6 mmol) in ethyl acetate at 0° C. was added triethylamine (17 mL, 122 mmol), followed by slow addition of a 50% solution of 1-propanephosphonic acid cyclic anhydride in ethyl acetate (18.1 mL, 30.5 mmol) and the reaction was allowed to warm to room temperature. After about 15 hours, the reaction was extracted from saturated aqueous sodium bicarbonate with ethyl acetate, the combined organics were washed with water and brine, dried ($MgSO_4$), concentrated in vacuo, and the product was purified by silica gel chromatography using 0% to 1% to 5% methanol in chloroform as eluant to give the title compound (19.5 g, 92%) as a colorless foam.

Step 9: 2-Amino-N-(1(R)-benzyloxymethyl-2-(1,3-dioxo-8a(S)-pyridin-2-ylmethyl-2-(2,2,2-trifluoro-ethyl)-hexahydro-imidazo[1,5-a]pyrazin-7-yl)-2-oxo-ethyl)-2-methyl-propionamide, hydrochloride The title compound of Step 8 (17.5 g, 25.3 mmol) was deprotected according to the method described in General Procedure A to afford a colorless solid. The product was triturated with diethyl ether to afford the title compound. (13.6 g, 90%): +APcI MS (M+H)$^+$ 591.

Preparation One 2-tert-Butoxycarbonylamino-2-methyl-propionic acid 2,5-dioxo-pyrrolidin-1-yl ester A stirred solution of N-hydroxysuccinimide (112 g, 0.973 mol), N-t-butoxycarbonyl-α-methylalanine (197 g, 0.969 mol), and 1-(3-dimethylaminopropyl)-3-ethyl-carbodiimide (186 g, 0.970 mol) in anhydrous dichloromethane (1.4 L) was stirred at room temperature for about 18 hours under nitrogen atmosphere. The reaction mixture was washed three times each with saturated sodium bicarbonate solution and then brine. The organic layer was dried over sodium sulfate, filtered and concentrated in vacuo to give the title compound of Preparation One as a white solid (256 g, 88%): PBMS (M+18)$^+$ 318; $^1$H NMR=250 MHz (CDCl$_3$) δ:4.91 (N$\underline{H}$, br s, 1H), 2.84 (—CO(C$\underline{H}_2$)$_2$CO—, s, 4H), 1.67 (Me, s, 6H), 1.48 (BOC, s, 9H).

Preparation Two

3-Benzyloxy-2-(2-tert-butoxycarbonylamino-2-methyl-propionylamino)-propionic acid To a solution of D-O-benzylserine (106 g, 0.532 mol) and the title compound of Preparation One (160 g, 0.532 mol) in water/dioxane (250/1000 mL) was slowly added triethylamine (223 mL, 1.60 mol) at room temperature. The reaction was heated to about 50° C. and stirred for about 15 hours under nitrogen atmosphere. The solvent was then removed in vacuo, ethyl acetate was added, and the stirred mixture was acidified with 10% aqueous HCl solution to pH 2–3. The organic layer was dried over sodium sulfate, filtered and concentrated in vacuo to give the title compound of Preparation Two (200 g, 99%): -APcI MS (M−1)$^-$ 379; $^1$H NMR=300 MHz (methanol-d$_4$) δ:7.69 (N$\underline{H}$, d, 1H), 7.32 (Ph, m, 5H), 4.60 (C$\underline{H}$CO$_2$H, m, 1H), 4.51 (C$\underline{H}_2$Ph, s, 2H), 3.81 (C$\underline{H}_2$OBz, m, 2H), 1.41 (Me, s, 6H), 1.40 (BOC, s, 9H).

What is claimed is:

1. A compound of Formula VII,

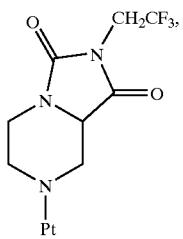

VII wherein
Pt is an amine protecting group.
2. A compound of claim 1 wherein Pt is Boc.

3. A process for preparing a compound of Formula XIII,

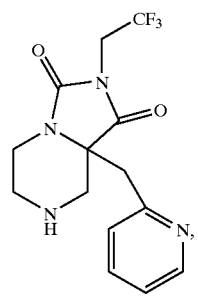

XIII comprising:
(a) reacting piperazine-1,3-dicarboxylic acid 1-tert-butyl ester 3-(C$_1$–C$_4$)alkyl ester with a carbonyl equivalent and 2,2,2-trifluoroethylamine in the presence of a reaction inert solvent to form the compound of Formula XIV,

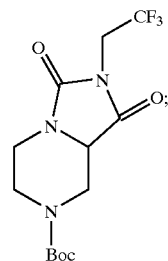

XIV (b) reacting said compound of Formula XIV with 2-picolyl-Z$^1$, wherein Z$^1$ is halo, methanesulfonyloxy or p-toluenesulfonyloxy, in the presence of a base and a reaction inert solvent to form the compound of Formula XV

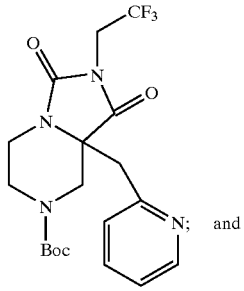

XV (c) reacting said compound of Formula XV with an acid in the presence a reaction inert solvent.

4. A process of claim 3, wherein in step (a), said carbonyl equivalent is N,N'-carbonyldiimidazole, phosgene, diphosgene or triphosgene and said reaction inert solvent is methylene chloride; in step (b), said alkylating agent is 2-picolyl chloride, said base is potassium bis(trimethylsilyl)amide, sodium bis(trimethylsilyl)amide, sodium amide, potassium amide, sodium (C$_1$–C$_4$)alkoxide or potassium (C$_1$–C$_4$) alkoxide and said reaction inert solvent is a mixture of tetrahydrofuran and N,N-dimethylformamide; and in step (c), said acid is methanesulfonic acid and said reaction inert solvent is methylene chloride.

5. A process of claim 4, wherein in step (a), said carbonyl equivalent is N,N'-carbonyldiimidazole; and in step (b), said base is potassium bis(trimethylsilyl)amide.

* * * * *